(12) United States Patent
Eder et al.

(10) Patent No.: US 9,700,265 B2
(45) Date of Patent: Jul. 11, 2017

(54) PATIENT SUPPORT APPARATUS

(71) Applicants: Hanns Eder, Bubenreuth (DE); Patrick Gross, Buckenhof (DE); Martin Ringholz, Erlangen (DE)

(72) Inventors: Hanns Eder, Bubenreuth (DE); Patrick Gross, Buckenhof (DE); Martin Ringholz, Erlangen (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 396 days.

(21) Appl. No.: 13/942,739

(22) Filed: Jul. 16, 2013

(65) Prior Publication Data
US 2014/0020180 A1  Jan. 23, 2014

(30) Foreign Application Priority Data

Jul. 17, 2012 (DE) .................. 10 2012 212 500

(51) Int. Cl.
*A61B 6/04* (2006.01)
*A61G 13/12* (2006.01)
*A61G 7/10* (2006.01)
*A61G 13/10* (2006.01)
*A61B 5/055* (2006.01)

(52) U.S. Cl.
CPC .......... *A61B 6/0421* (2013.01); *A61B 5/0555* (2013.01); *A61G 7/103* (2013.01); *A61G 7/1034* (2013.01); *A61G 13/10* (2013.01); *A61G 13/121* (2013.01)

(58) Field of Classification Search
CPC .......... A47C 20/00; A47C 20/02; A61B 5/70; A61B 5/702; A61B 5/704; A61B 5/706; A61B 6/04; A61B 6/0407; A61B 6/0421; A61B 6/0428; A61B 6/0442; A61B 6/0492; A61B 5/0555; A61G 7/0526; A61G 7/07; A61G 7/072; A61G 13/121; A61G 7/103; A61G 7/1034; A61G 13/10
See application file for complete search history.

(56) References Cited

U.S. PATENT DOCUMENTS

| 4,064,401 A * | 12/1977 | Marden ................ A61B 6/501 378/208 |
| 6,003,174 A | 12/1999 | Dinkler |
| 2002/0032927 A1* | 3/2002 | Dinkler ................ A61B 6/0442 5/601 |

(Continued)

FOREIGN PATENT DOCUMENTS

| CN | 201005699 Y | 1/2008 |
| CN | 201227382 Y | 4/2009 |
| DE | 102006022297 A1 | 5/2007 |

*Primary Examiner* — Nicholas Polito

(57) ABSTRACT

A patient support apparatus is provided. The patient support apparatus may be used as an operating table apparatus for a neurosurgical intervention. The patient support apparatus includes a support couch and a transfer plate which may be moved relative to the support couch, wherein the transfer plate is designed to support a patient for the neurosurgical intervention, wherein the patient support apparatus includes a holding unit with a support shell, which is designed to support a head of the patient and/or a surgical head restraint unit, and a fastening unit for fastening the holding unit to the patient support apparatus.

9 Claims, 2 Drawing Sheets

(56) References Cited

U.S. PATENT DOCUMENTS

| | | | |
|---|---|---|---|
| 2006/0293589 A1* | 12/2006 | Calderon | A61G 7/1019 600/415 |
| 2007/0055145 A1* | 3/2007 | Zelnik | A61B 6/5235 600/428 |
| 2010/0106165 A1* | 4/2010 | Jacob | A61B 6/0421 606/130 |
| 2010/0249575 A1* | 9/2010 | Shvartsberg | G01R 33/30 600/415 |

* cited by examiner

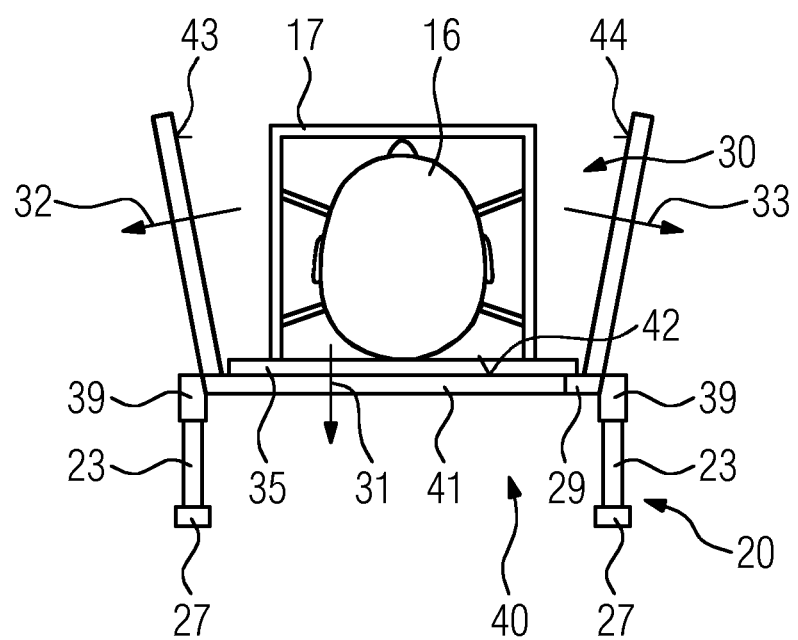

PATIENT SUPPORT APPARATUS

CROSS REFERENCE TO RELATED APPLICATIONS

The present application claims priority to German application No. 10 2012 212500.0 DE filed Jul. 17, 2012, the entire content of which is hereby incorporated herein by reference.

FIELD OF INVENTION

The present invention relates to a patient support apparatus, in particular an operating table apparatus for a neurosurgical intervention, having a support couch and a transfer plate which can be moved relative to the support couch, wherein the transfer plate is configured to support a patient for the neurosurgical intervention.

BACKGROUND OF INVENTION

For neurosurgical interventions, the patient is positioned on a patient support apparatus, in particular an operating table apparatus. Here the patient is positioned on a transfer plate, since a medical imaging examination, for instance a magnetic resonance examination, of the head region of the patient, is frequently implemented during an interruption in the neurosurgical intervention and/after the neurosurgical intervention has concluded. The patient is switched in such cases between the operating table and a further patient support apparatus, which is embodied to be magnetic resonance-compatible for a magnetic resonance examination, by means of the transfer plate. A surgical head restraint unit is attached to the patient, in particular to the head of the patient and/or the head of the patient is positioned within this surgical head restraint unit for the neurosurgical intervention, wherein the surgical head restraint unit is arranged for instance on the transfer plate and protrudes beyond the transfer plate together with the head of the patient.

A maximum permissible area of occupation is available for the surgical head restraint unit, which is measured in particular in accordance with a cross-sectional surface of a patient receiving area of the medical imaging apparatus. If the surgical head restraint unit protrudes beyond the area of occupation which is permissible for the surgical head restraint unit, upon insertion of the patient positioned on the transfer plate together with the surgical head restraint unit, this may result in unwanted collisions with in particular a housing of the medical imaging apparatus. The risk of injury to the patient herewith increases. In addition, the surgical head restraint unit must be repositioned in order to be able to record a medical imaging examination at all. This repositioning may result in unwanted delays, since a sterile cover of the surgical head restraint unit must firstly be dismantled for the repositioning.

The positioning of the surgical head restraint unit and/or of the head of the patient is implemented by a surgeon and/or clinical operating personnel, wherein this positioning is very complicated. In addition, this positioning takes place with the aid of a rough estimation of the permissible area of occupation and/or in accordance with empirical values of the surgeon and/or the operating personnel. This may however result in only a fraction of the permissible area of occupation being used for instance or collisions possibly resulting upon insertion into the medical imaging apparatus.

SUMMARY OF INVENTION

The object underlying the present invention is in particular to provide a patient support apparatus, in which a time-saving and simple fixing and/or positioning of the head of the patient within the surgical head restraint unit can be achieved. The object is achieved by the features of the independent claims. Advantageous embodiments are described in the subclaims.

The invention is based on a patient support apparatus, in particular an operating table apparatus for a neurosurgical intervention, having a support couch and a transfer plate which can be moved in respect of the support couch, wherein the transfer plate is configured to support a patient for a neurosurgical intervention.

It is proposed that the patient support apparatus comprises a holding unit with a support shell, which is configured to support a head of the patient and/or a surgical head restraint unit, and a fastening unit for fastening the holding unit to the patient support apparatus. The head of the patient can advantageously be supported here on the support shell particularly during a positioning of the surgical head restraint unit and/or during a positioning of the head of the patient and a time-saving and in particular simple positioning for clinical operating personnel, for instance a surgeon, can thus be achieved. In addition, stress on the patient during the positioning of the head of the patient and/or the surgical head restraint unit can be reduced by means of the holding unit with the support shell. In this context, a transfer plate is in particular to be understood to mean a support plate for directly supporting the patient for a surgical intervention and/or a medical imaging examination, wherein the transfer plate can be switched between at least two patient support apparatuses, for instance an operating table and a moveable and/or mobile patient support apparatus, which is configured for transporting the patient and which is preferably configured for docking to the medical imaging apparatus. The transfer plate is to this end advantageously embodied for use in conjunction with a medical imaging apparatus, wherein the patient lying on the transfer plate can be moved and/or introduced into a patient receiving area of the medical imaging apparatus for a medical imaging examination. The medical imaging apparatus can here include a magnetic resonance apparatus and/or a computed tomography apparatus and/or a PET (Positron-Emission-Tomography)-apparatus and/or a mobile or fixed x-ray-based C-arm system and/or a SPECT (single photon emission computed tomography) apparatus. An additional support element is preferably arranged on the support shell, such as for instance a support and/or a gel pad and/or gel cushions, as a result of which comfortable support of the head of the patient can be achieved.

It is further proposed that the support shell can be fastened by means of the fastening unit such that the support shell delimits and/or marks a maximum permissible area of occupation for the surgical head restraint unit in at least one direction. An unwanted incorrect positioning and/or also a repositioning of the surgical head restraint unit to be performed on account of the incorrect positioning can herewith be advantageously prevented and a risk of infection to the patient can thus also be minimized. Furthermore, a simple and comfortable positioning of the surgical head restraint unit can also be enabled for the clinical operating personnel. The maximum permissible area of occupation for the surgical head restraint unit is here provided and/or delimited by a patient receiving area of the medical imaging apparatus, for instance a magnetic resonance apparatus, wherein the maximum permissible area of occupation is formed by a cross-sectional surface of the patient area of occupation less a safety margin and/or tolerance range.

It is further proposed that the support shell be embodied in the manner of a plate, as a result of which the support shell also makes available a sufficiently large space for the surgical head restraint unit and/or the subsequent neurosurgical intervention. Furthermore, a restriction in the area of occupation permissible for the surgical head restraint unit can be indicated by means of the plate-shaped support shell for the positioning of the surgical head restraint unit and/or of the head of the patient in at least one direction, in particular a direction of force of gravity acting on the patient support apparatus, and an incorrect positioning of the surgical head restraint device is particularly advantageously prevented in this way. The plate-shaped support shell advantageously delimits and/or marks the maximum permissible area of occupation in a critical collision area of the surgical head restraint unit with the medical imaging apparatus, in particular with a housing of the medical imaging apparatus surrounding the patient receiving area.

In an alternative embodiment of the invention, it is proposed to embody the support shell in a U shape, as a result of which the area of occupation permissible for the surgical head restraint unit can, particularly advantageously, be delimited and/or marked in a number of directions, in particular in a peripheral direction about the head and/or about the surgical head restraint unit so that a particularly time-saving and comfortable positioning of the head of the patient and/or the surgical head restraint unit can be achieved.

A particularly compact holding unit and/or support shell, which also provides unhindered access to the clinical operating personnel for the imminent surgical intervention on the patient, can be advantageously achieved if the holding unit comprises at least one U-shaped molded part, which can be attached to the support shell and delimits and/or marks a maximum permissible area of occupation for the surgical head restraint unit in at least one direction. The U-shaped molded part is preferably only arranged for the positioning of the surgical head restraint unit and an alignment and/or positioning of the head for the imminent surgical intervention on the support shell and is then removed and/or dismantled from the support shell. To this end, the U-shaped molded part for the positioning of the head of the patient and/or the surgical head restraint unit can be moved particularly easily between a support surface of the support shell and the head of the patient. The U-shaped molded part and/or the support shell can to this end also comprise fastening elements, such as for instance locking elements etc., which fasten and/or fix the U-shaped molded part to the support shell for the duration of the positioning of the head of the patient and/or the surgical head restraint unit, so that an unwanted slipping of the U-shaped molded part during the positioning of the surgical head restraint unit can also be advantageously prevented.

In an advantageous development of the invention, it is proposed that the fastening unit has a fastening element for a removable fastening to the support couch and/or the transfer plate, as a result of which the holding unit can only be fastened to the patient support apparatus, in particular to the support couch and/or the transfer plate, for neurosurgical interventions in which a head restraint unit is required. The holding unit is nevertheless particularly advantageously arranged on the support couch so that the transfer plate can be switched and/or transferred particularly easily between conventional support couches of patient support apparatuses, in particular patient transport support apparatuses. Furthermore, an unintentional collision between the holding unit arranged on the transfer plate and a support couch can in this way advantageously be prevented during a transfer of the transfer plate.

A particularly simple and time-saving fastening of the holding unit to the support couch can be achieved if the fastening element is embodied so as to correspond to a fastening rail of the support couch. In addition, a particularly cost-effective embodiment of the patient support apparatus can be achieved here, since the holding unit can be attached and/or fastened to a fastening element of the support couch which is already present. The fastening element can be formed here by a fastening clamp and/or fastening screw etc. which can be fastened in the fastening rail of the support couch. The support couch of the patient support apparatus comprises laterally arranged fastening rails for fastening and/or receiving additional units, for instance an infusion unit etc, which can be used particularly advantageously for fastening the holding unit.

The fastening unit advantageously comprises a stop element for positioning the holding unit in respect of the support couch, so that a position of the support shell set in respect of the support couch can advantageously be retained and a complicated repositioning of the support shell can advantageously be omitted here. The stop element can be formed here by locking screws and/or further stop elements which appear meaningful to the person skilled in the art.

In an advantageous development of the invention, it is proposed that the holding unit comprises at least one adjustment element, as a result of which a particularly simple and time-saving adjustment of the holding unit, in particular of the support shell, can be achieved. The adjustment element may include for instance a spirit level and/or further adjustment elements which appear meaningful to the person skilled in the art.

It is further proposed that the holding unit comprise a joint unit, as a result of which the support shell can in particular be especially easily positioned and/or mounted in a space-saving manner on the support couch and/or the transfer plate when not in use. This position of the support shell advantageously prevents an impairment and hindrance of clinical operating personnel. In addition, the joint unit also introduces the support shell for a neurosurgical intervention particularly quickly into an operating position provided therefor by the clinical operating personnel. The joint unit is preferably coupled to a stop element of the holding unit so that the desired position of the support shell can be particularly easily fixed by the clinical operating personnel. Provision can also be made for the support shell to be mounted so as to be moveable between two or more stop positions by means of the joint unit, so that a particularly simple adjustment of a desired position of the support shell can be achieved for the clinical operating personnel. The joint unit may comprise a swivel joint unit and/or a ball joint unit and/or a universal joint unit and/or further joint units which appear meaningful to the person skilled in the art.

A particularly advantageous use of the holding unit together with a magnetic resonance apparatus can be achieved if the holding unit is embodied to be magnetic resonance-compatible. Furthermore, it is advantageous if the holding unit, in particular the support shell and/or the U-shaped molded part of the holding unit, is formed from a robust material which is easy to clean.

BRIEF DESCRIPTION OF THE DRAWINGS

Further advantages, features and details of the invention result from the exemplary embodiments described below and with the aid of the drawings, in which:

FIG. 2 shows a schematic section through a first support shell of the patient support apparatus and FIG. 3 shows a schematic section through a second support shell of the patient support apparatus.

DETAILED DESCRIPTION OF INVENTION

Figure 1:
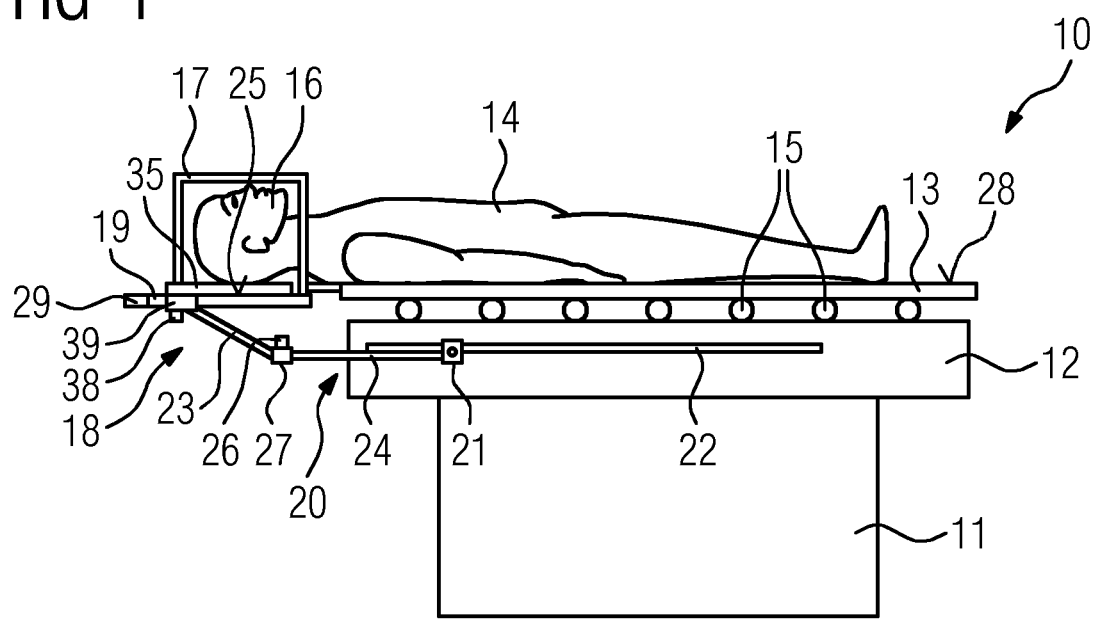
FIG. 1 shows a first view of an inventive patient support apparatus in a schematic representation.

An inventive patient support apparatus 10 is shown schematically in FIG. 1. In the present exemplary embodiment, the patient support apparatus 10 is formed by an operating table apparatus which is designed in particular for a neurosurgical intervention. The patient support apparatus 10 can basically also be formed by a patient support apparatus 10 which is embodied as an alternative to an operating table apparatus.

The patient support apparatus 10 includes a base unit 11 and a support couch 12, wherein the support couch 12 is arranged on the base unit 11. Furthermore, the patient support apparatus 10 includes a transfer plate 13, which is configured for supporting and/or positioning a patient 14 for the neurosurgical intervention. To this end, the patient support apparatus 10 comprises support elements, in particular sliding bearing elements 15, for moveable support of the transfer plate 13 in respect of the support couch 12. The sliding bearing elements 15 here may include roller bearing elements etc. Furthermore, the patient support apparatus 10 includes a stop unit (not shown in more detail) for stopping the transfer plate 13 with the support couch 12, so that a fixed positioning of the transfer plate 13 on the support couch 12 is provided for a surgical intervention.

The transfer plate 13 can be switched between different patient support apparatuses 10. For instance, a medical imaging examination takes place during an interruption in the neurosurgical intervention and/or following the neurosurgical intervention, wherein to this end the patient 14 is firstly transferred lying on the transfer plate 13 onto a further patient support apparatus. This further patient support apparatus can be designed for instance to be dockable to the medical imaging apparatus, for instance a magnetic resonance apparatus, so that the patient 14, together with the transfer plate 14, can be moved and/or introduced within a patient receiving area of the medical imaging apparatus for the medical imaging examination.

Figure 2:
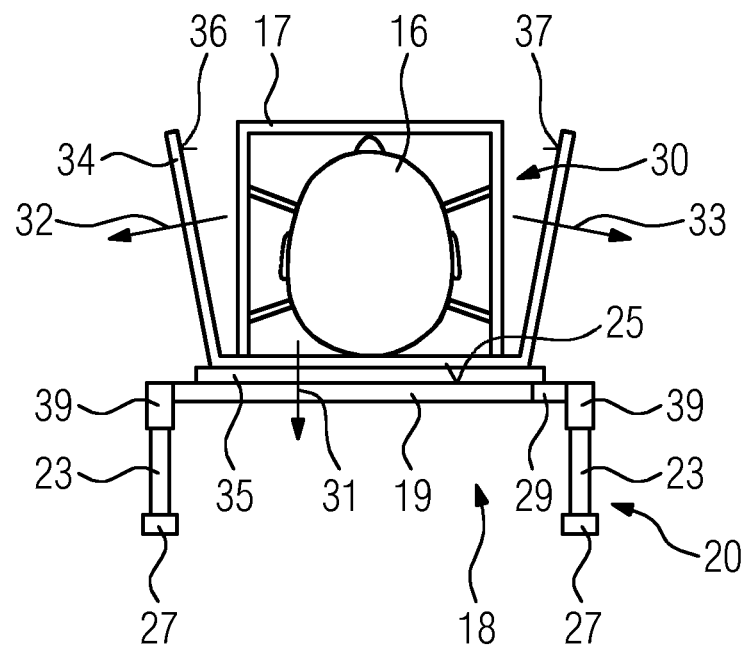

For the neurosurgical intervention, a head 16 of the patient 14 is positioned within a surgical head restraint unit 17. The surgical head restraint unit 17 is preferably embodied to be magnetic resonance-compatible. The patient support apparatus 10 comprises a holding unit 18 for a time-saving and comfortable positioning of the head 16 of the patient 14 within the surgical head restraint unit 17 (FIGS. 1 and 2). The holding unit 18 includes a support shell 19 for supporting the head 16 of the patient 15 and/or the surgical head restraint unit 17. Furthermore, the holding unit 18 includes a fastening unit 20 for fastening the mounting shell 19 on the patient support apparatus 10, in particular on the support couch 12 and/or on the transfer plate 13. In the present exemplary embodiment the fastening unit 20 is embodied so as to fasten to the support couch 12. Basically the fastening unit 20 can also be embodied to fasten to the transfer plate 13.

A support element 35 of the patient support apparatus 10 for supporting the head 16 of the patient 14 is arranged on the support shell 19 in the present exemplary embodiment, thereby at least partially enabling comfortable support of the patient 14. The support element 35 may for instance be formed by a gel cushion and/or a gel pad etc.

The fastening unit 20 comprises fastening elements 21 for fastening to the support couch 12, said fastening elements 21 being embodied so as to correspond to fastening rails 22 of the support couch 12. The fastening rails 22 are arranged laterally on the support couch 12 for receiving and/or fastening additional units, such as in particular infusion units etc. In addition to the additional units, the holding unit 18 is also fastened to the fastening rails 22 by means of the fastening unit 20. To this end, the fastening unit 20 comprises at least one fastening element 21, by means of which the holding unit 18, in particular the support shell 19, can be removably fastened to the support couch 12. The fastening element 21 may here include a fastening clamp and/or a fastening screw. The fastening unit 20 preferably comprises two fastening elements 21, so that the support shell 19 can be fastened to the support couch 12 on both sides using a fastening rail 22 of the support couch 12 in each instance (FIGS. 1 and 2).

The fastening unit 20 also comprises connecting elements 23, 24, which are arranged between the fastening elements 21 and the support shell 19. The connecting elements 23, 24 are embodied in the manner of bars. In addition, two of the connecting elements 23 are arranged in each instance laterally on the support shell 19, in each instance adjacent to a support surface 25 and/or a support area of the support shell 19, wherein the two connecting elements 23 are arranged on opposing sides of the support shell 19 (FIGS. 1 and 2).

Furthermore, the fastening unit 20 comprises stop elements 26 38 and joint units 27, 39. The support shell 19 can be adjusted in terms of height with regards to a support surface 28 of the transfer plate 13 by means of the joint units 27, 39 and the stop elements 26, 38, wherein the position of the support shell 19 can be selected by means of the joint units 27, 39 and a selected position of the support shell 19 can be fixedly stopped by means of the stop elements 26, 38. In order to set the height of the support surface 25 of the support shell 19, the joint units 39 are arranged on the support shell 19 and connect the support shell 19 to the carrier elements 23. Furthermore joint units 27 are arranged between the two carrier elements 23, 24. The stop elements 26, 38 are arranged in each instance on one of the joint units 27, 39 relative to a stop of a position of the support shell 19 (FIG. 1) set by means of the joint units 27, 39.

The joint units 27, 39 may each include a rotary joint unit and/or a spherical joint unit and/or a cross joint unit and/or further joint units which appear meaningful to the person skilled in the art.

For setting and/or positioning purposes, the holding unit 18 further comprises an adjustment element 29, which is arranged on the support shell 19. An alignment of the support shell 19 can be correctly set by the clinical operating personnel during the positioning process by means of the adjustment element 29, so that the support surface 25 of the support shell 19 assumes a correct position. The adjustment element 29 may be formed for instance by a spirit level and/or further adjustment elements which appear meaningful to the person skilled in the art.

The support shell 19 of the holding unit 18 comprises a form which delimits and/or marks (FIG. 2) a maximum area of occupation 30 of the surgical head restraint unit 17 in at least one direction 31. The maximum area of occupation 30 for the surgical head restraint unit 17 is determined by a patient receiving area of the medical imaging apparatus. The maximum area of occupation 30 for the surgical head restraint unit 18 is determined by a cross-sectional surface of the patient receiving area minus a safety margin and/or a tolerance range, so that when introducing the patient 14, together with the surgical head restraint unit 17, into the patient receiving area, a collision of the surgical head restraint unit 17 with a housing of the medical imaging apparatus can be reduced and/or prevented.

The support surface 28 of the transfer plate 13, on which the patient 14 is moved into the patient receiving area, is used as a reference value for the maximum receiving area 30, since a position of the transfer plate 13 within the cross-sectional surface of the patient receiving area is known. Based on this position of the support surface 28 of the transfer plate 13, the support shell 19 is arranged on the support couch 12 such that the support shell 19, in particular a support surface 25 of the support shell 19 for supporting the head 16 of the patient 14, delimits and/or marks the maximum receiving area 30 downwards and/or in a direction 31 of a force of gravity acting on the patient support apparatus 10. The support shell 19 thus represents a lower limit and/or a limit in the direction 31 of the force of gravity acting on the patient support apparatus 10 (FIG. 2).

The support shell 19 in FIG. 2 is embodied in the manner of a plate so that the plate-shaped support shell 19 marks and/or delimits the lower limit and/or a limit in the direction 30 of the force of gravity acting on the patient support apparatus 10. For a positioning of the head 16 of the patient 14 within the surgical head restraint unit 17 and/or a positioning of the head 16 of the patient 14 for the surgical intervention, the surgical head restraint unit 17 can thus not protrude beyond the support shell 19 along the force of gravity acting on the patient support apparatus 10 so that the surgical head restraint unit 17 is not able to protrude from the maximum permissible area of occupation 30 in this direction 31.

In order also to increase protection and/or safety against collisions during insertion of the patient 12 together with the surgical head restraint unit 17 into the patient receiving area, the holding unit 18 also comprises a U-shaped molded part 34, which can be arranged on the support shell 19 for a positioning of the head 16 of the patient 14 and/or the surgical head restraint unit 17. The U-shaped molded part 34 can be introduced here between the support surface 25 of the support shell 19 and/or the support element 35 and the head 16 of the patient 14 and/or the surgical head restraint unit 17. For the positioning of the head 16 of the patient 14 and/or the surgical head restraint unit 17, provision can also be made for the U-shaped molded part 34 and/or the support shell 19 to comprise fastening elements (not shown) for a secure and in particular non-slippable positioning of the U-shaped molded part 34 on the support shell 19.

The U-shaped molded part 34 here comprises a U-shaped shell form, wherein a lateral delimiting and/or marking of the maximum permissible area of occupation 30 for the surgical head restraint unit 17 is shown by the U-shaped shell form. Lateral marking surfaces 36, 37 and/or delimiting surfaces of the U-shaped molded part 34 essentially extend in parallel to a longitudinal extension of the transfer plate 13 and essentially in parallel to the force of gravity acting on the patient support apparatus 10 (FIG. 2). A delimiting and/or marking of the maximum permissible area of occupation 30 takes place in two further directions 32, 33 by means of the two marking surfaces 36, 37, said two further directions essentially being aligned at right angles to the two marking surfaces 36, 37.

After the positioning of the head 16 of the patient 14 and/or the surgical head restraint unit 17 is concluded, the U-shaped molded part 34 is removed again from the support shell 19 by the clinical operating personnel, so that an advantageous, in particular free, accessibility to the head 16 of the patient 14 is provided for the surgical intervention.

An alternative embodiment of the holding unit 40 to that in FIG. 2 is shown in FIG. 3. The subsequent description is essentially restricted to the differences in respect of the exemplary embodiment in FIGS. 1 and 2, wherein reference is made to the description of the exemplary embodiment in FIGS. 1 and 2 with respect to the identical components, features and functions. Essentially identical components, features and functions are basically numbered with the same reference characters.

The holding unit 40 in FIG. 3 differs from the holding unit 18 from FIG. 2 in an embodiment of the support shell 41. The support shell 41 of the holding unit 40 from FIG. 3 is embodied to be U-shaped, wherein the U-shaped support shell 41 here assumes a function of the plate-shaped support shell 19 and of the U-shaped molded part 34 from FIG. 2. The U-shaped support shell 41 to this end comprises a support surface 42 and two lateral delimiting walls 43, 44, which each mark and/or delimit the maximum permissible area of occupation 30 for the surgical head restraint unit 17.

The further embodiment of the holding apparatus 40, in particular an embodiment of a fastening unit 20 of the fastening unit, is embodied in a similar manner to the description with respect to the exemplary embodiment in FIGS. 1 and 2, so that a fastening of the holding apparatus 40 to the support couch 12 of the patient support apparatus 10 also takes place in a similar manner to the description relating to FIGS. 1 and 2.

Irrespective of an embodiment of the holding unit 18, 40 and/or the support shell 19, 41, the holding unit 18, 40 is preferably embodied to be magnetic resonance-compatible for a use of the holding unit 18, 40 together with a medical imaging apparatus formed by a magnetic resonance apparatus. In addition, the holding unit 18, 40, in particular the support shell 19, 41, is formed from a robust material which is nevertheless easy to clean.

We claim:

1. A patient support apparatus, comprising:
   a support couch;
   a transfer plate which is moved relative to the support couch; and
   a holding unit,
   wherein the transfer plate is embodied to support a patient for a neurosurgical intervention,
   wherein the holding unit includes a support shell, which is configured to support a head of the patient, a surgical head restraint unit, and a fastening unit for fastening the holding unit to the patient support apparatus,
   wherein the fastening unit comprises a joint arranged on the support shell,
   wherein the joint is configured to adjust a height of the support shell with respect to a support surface of the transfer plate,
   wherein the holding unit comprises a U-shaped molded part which is arranged between the support shell and the surgical head restraint unit,
   wherein the U-shaped molded part is removed from the holding unit after positioning the surgical head restraint unit,
   wherein the U-shaped molded part comprises two lateral surfaces that extend in a direction essentially in parallel to a direction of force of gravity acting on the patient support apparatus,
   wherein the U-shaped molded part is arranged on a support surface of the support shell, and wherein the two lateral surfaces of the U-shaped molded part and the support surface of the support shell mark a maximum permissible area of occupation for the surgical head restraint unit in a vertical plane.

2. The patient support apparatus as claimed in claim 1, wherein the support shell is embodied in the manner of plate.

3. The patient support apparatus as claimed in claim 1, wherein the support shell is embodied to be U-shaped.

4. The patient support apparatus as claimed in claim 1, wherein the fastening unit comprises a fastening element for a removable fastening of the holding unit on the support couch and the transfer plate.

5. The patient support apparatus as claimed in claim 4, wherein the fastening element is embodied so as to correspond with a fastening rail of the support couch.

6. The patient support apparatus as claimed in claim 4, wherein the fastening unit comprises a stop element for positioning the holding unit in respect of the support couch.

7. The patient support apparatus as claimed in claim 1, wherein the fastening unit comprises a fastening element for a removable fastening of the holding unit on the support couch or the transfer plate.

8. The patient support apparatus as claimed in 1, wherein the holding unit comprises an adjustment element.

9. The patient support apparatus as claimed in claim 1, wherein the holding unit is embodied to be magnetic resonance-compatible.

* * * * *